(12) United States Patent
Linder et al.

(10) Patent No.: US 8,798,742 B2
(45) Date of Patent: **\*Aug. 5, 2014**

(54) METHOD AND APPARATUS FOR ADJUSTING CARDIAC EVENT DETECTION THRESHOLD BASED ON DYNAMIC NOISE ESTIMATION

(75) Inventors: William J. Linder, Golden Valley, MN (US); Jeremy Maniak, Columbia Heights, MN (US); Ron A. Balczewski, Bloomington, MN (US)

(73) Assignee: Cardiac Pacemakers, Inc., St. Paul, MN (US)

( \* ) Notice: Subject to any disclaimer, the term of this patent is extended or adjusted under 35 U.S.C. 154(b) by 454 days.

This patent is subject to a terminal disclaimer.

(21) Appl. No.: 12/415,619

(22) Filed: Mar. 31, 2009

(65) Prior Publication Data

US 2009/0192563 A1 Jul. 30, 2009

Related U.S. Application Data

(63) Continuation of application No. 11/557,318, filed on Nov. 7, 2006, now Pat. No. 7,515,955, which is a continuation of application No. 10/967,660, filed on Oct. 18, 2004, now Pat. No. 7,155,275.

(51) Int. Cl.
*A61N 1/39* (2006.01)
*A61B 5/0428* (2006.01)

(52) U.S. Cl.
USPC ............................................. 607/5; 600/509

(58) Field of Classification Search
USPC ........... 600/411, 509; 128/901, 902; 607/2, 4, 607/5, 9
See application file for complete search history.

(56) References Cited

U.S. PATENT DOCUMENTS

| | | | |
|---|---|---|---|
| 4,291,699 A * | 9/1981 | Geddes et al. | ................... 607/6 |
| 4,991,587 A | 2/1991 | Blakeley et al. | |
| 5,188,117 A | 2/1993 | Steinhaus et al. | |
| 5,564,430 A | 10/1996 | Jacobson et al. | |
| 5,620,466 A | 4/1997 | Haefner et al. | |
| 5,658,317 A | 8/1997 | Haefner et al. | |
| 5,662,688 A | 9/1997 | Haefner et al. | |
| 5,702,425 A | 12/1997 | Wickham | |
| 5,755,738 A | 5/1998 | Kim et al. | |

(Continued)

OTHER PUBLICATIONS

"U.S. Appl. No. 10/967,660, Notice of Allowance mailed Jun. 13, 2006", 8 pgs.

(Continued)

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

An implantable cardiac rhythm management (CRM) device includes a sensing and detection circuit that senses at least one cardiac signal and detects cardiac electrical events from the sensed cardiac signal using a detection threshold that is adjusted based on a dynamic noise estimation. The sensed cardiac signal is filtered to produce a filtered cardiac signal having a signal frequency band and a noise signal having a noise frequency band. The noise frequency band is substantially different from the signal frequency band. A dynamic noise floor is produced based on the noise signal and used as the minimum value for the detection threshold. A cardiac electrical is detected when the amplitude of the filtered cardiac signal exceeds the detection threshold.

19 Claims, 6 Drawing Sheets

(56) References Cited

U.S. PATENT DOCUMENTS

| | | | |
|---|---|---|---|
| 5,873,836 A * | 2/1999 | Kahn et al. | 600/493 |
| 5,891,171 A | 4/1999 | Wickham | |
| 5,957,857 A | 9/1999 | Hartley | |
| 6,029,086 A | 2/2000 | Kim et al. | |
| 6,112,119 A | 8/2000 | Schuelke et al. | |
| 6,324,421 B1 * | 11/2001 | Stadler et al. | 600/509 |
| 6,418,343 B1 | 7/2002 | Zhang et al. | |
| 6,434,417 B1 | 8/2002 | Lovett | |
| 6,434,426 B1 | 8/2002 | Munneke et al. | |
| 6,493,584 B1 | 12/2002 | Lu | |
| 6,584,351 B1 | 6/2003 | Ekwall | |
| 7,155,275 B2 | 12/2006 | Linder et al. | |
| 2003/0083538 A1 | 5/2003 | Adams et al. | |
| 2003/0083583 A1 | 5/2003 | Kovtun et al. | |
| 2003/0187354 A1 * | 10/2003 | Rust et al. | 600/437 |
| 2004/0106957 A1 | 6/2004 | Palreddy et al. | |
| 2004/0193223 A1 * | 9/2004 | Kramer et al. | 607/9 |
| 2004/0267148 A1 * | 12/2004 | Arand et al. | 600/528 |
| 2007/0088399 A1 | 4/2007 | Linder et al. | |

OTHER PUBLICATIONS

"U.S. Appl. No. 11/557,318, Notice of Allowance mailed Nov. 21, 2008", 8 pgs.

* cited by examiner

METHOD AND APPARATUS FOR ADJUSTING CARDIAC EVENT DETECTION THRESHOLD BASED ON DYNAMIC NOISE ESTIMATION

CROSS REFERENCE TO RELATED APPLICATION(S)

This application is a continuation of U.S. patent application Ser. No. 11/557,318, filed on Nov. 7, 2006, now issued as U.S. Pat. No. 7,515,955, which is a continuation of U.S. patent application Ser. No. 10/967,660, filed on Oct. 18, 2004, now issued as U.S. Pat. No. 7,155,275, the specifications of which are incorporated herein by reference.

FIELD OF THE INVENTION

This document generally relates to a cardiac rhythm management (CRM) systems and particularly, but not by way of limitation, to an implantable CRM device including a sensing and detection circuit that detects cardiac electrical events using a detection threshold that is adjusted based on dynamic noise estimation.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. In a normal heart, the sinoatrial node, the heart's natural pacemaker, generates electrical impulses, known as action potentials, that propagate through an electrical conduction system to various regions of the heart to cause the depolarization of the electrical conduction system and excitation of myocardial tissues in these regions. Coordinated delays in the propagations of the electrical impulses in a normal electrical conduction system cause the various regions of the heart to contract in synchrony such that the pumping functions are performed efficiently. Arrhythmia occurs, for example, when the sinoatrial node fails to generate the electrical impulses at a normal rate, when electrical impulses are generated from a pathological origin, and/or when pathological changes occur to the electrical conduction system. Arrhythmia causes the heart to contract at a rhythm that is too slow, too fast, or irregular. Consequently, the heart's pumping efficiency is reduced, and hence, the blood flow to the body is diminished.

Implantable CRM devices are used to treat arrhythmias by delivering electrical pulses to the patient's heart. In one example, pacing pulses are delivered to one or more regions of the heart to at least partially restore the function of the sinoatrial node and/or the electrical conduction system. According to many pacing algorithms, a pacing pulse is delivered on demand, i.e., when a corresponding intrinsic depolarization is absent or abnormally delayed. In another example, a defibrillation pulse is delivered to the heart to stop a rhythm that is too fast and/or irregular. This requires detection of a depolarization rate and/or pattern that warrant a delivery of the defibrillation pulse. Thus, the detection of cardiac electrical events including depolarizations is important in both pacing and defibrillation therapies.

The cardiac depolarizations are detected from one or more cardiac signals each sensed with at least one electrode placed in or on the heart. In addition to cardiac depolarizations, noises of various types are often present in such cardiac signals. The sources of such noises include, but not limited to, non-cardiac bioelectric activities such as myoelectrical signals associated with breathing and/or bodily movements and interference from nearby electrical power lines, equipment, and appliances. An implantable CRM device detects a cardiac depolarization when the amplitude of a cardiac signal exceeds a detection threshold. When the threshold is set low, the noises may cause over-sensing, i.e., the implantable CRM device detects noise as cardiac depolarizations. Consequently, the implantable CRM device fails to deliver pacing pulses when needed and/or delivers a defibrillation pulse that is not needed. When the threshold is set high to avoid detection of noise, under-sensing may occur, i.e., the implantable CRM device fails to detect cardiac depolarizations. Consequently, the implantable CRM device delivers of pacing pulses that are not needed or not properly timed based to the heart's intrinsic activities and/or fails to deliver a defibrillation pulse when fibrillation occurs. Depending on the type of therapy, over-sensing and under-sensing both have consequences ranging from inefficient therapy to death. For example, the consequence of a failure to deliver a defibrillation pulse may be fatal, while the consequence of a delivering an unnecessary defibrillation pulse causes significant discomfort to the patient and shortens the life expectancy of the implantable CRM device. For these and other reasons, there is a need to provide an acceptably accurate detection of cardiac electrical events in the presence of noise.

SUMMARY

An implantable CRM device includes a sensing and detection circuit that senses at least one cardiac signal and detects cardiac electrical events from the sensed cardiac signal using a detection threshold that is adjusted based on dynamic noise estimation. The sensed cardiac signal is filtered to produce a filtered cardiac signal having a signal frequency band and a noise signal having a noise frequency band. The noise frequency band is substantially different from the signal frequency band. A dynamic noise floor is produced based on the noise signal and used as the minimum value for the detection threshold. A cardiac electrical is detected when the amplitude of the filtered cardiac signal exceeds the detection threshold.

In one embodiment, a cardiac sensing system includes a sensing circuit, a noise estimation circuit, and an event detection circuit. The sensing circuit senses a cardiac signal and includes a signal filter to produce a filtered cardiac signal based on the cardiac signal. The filtered cardiac signal has a signal frequency band. The noise estimation circuit includes a noise filter and a noise floor generator. The noise filter produces a noise signal based on the cardiac signal. The noise signal has a noise frequency band that is substantially different from the signal frequency band. The noise floor generator produces a dynamic noise floor based on the noise signal. The event detection circuit includes a threshold circuit and a comparator. The threshold circuit dynamically produces a detection threshold based on at least the amplitude of the filtered cardiac signal and the dynamic noise floor. The comparator compares the filtered cardiac signal to a detection threshold and indicates a detection of a cardiac electrical event when the amplitude of the filtered cardiac signal exceeds the detection threshold.

In one embodiment, an implantable CRM device includes one or more sensing channels, a therapy output circuit, and an implant control circuit, contained in an implantable housing. Each sensing channels includes a circuit of the cardiac sensing system. The therapy output circuit delivers one or more cardiac therapies. The implant control circuit controls the delivery of the one or more cardiac therapies in response to one or more cardiac electrical events detected by the one or more sensing channels.

In one embodiment, a method for detecting cardiac electrical events is provided. A cardiac signal is sensed. The cardiac signal is filtered to produce a filtered cardiac signal for detecting the cardiac electrical events in a signal frequency band and also filtered to produce a noise signal for measuring a noise level in a noise frequency band. A dynamic noise floor is produced based on the noise signal. A dynamic detection threshold is produced based on the amplitude of the filtered cardiac signal and the dynamic noise floor. Cardiac electrical events are detected by comparing the amplitude of the filtered cardiac signal to the dynamic detection threshold.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings, which are not necessarily drawn to scale, illustrate generally, by way of example, but not by way of limitation, various embodiments discussed in the present document.

FIG. 2 is a graph illustrating a filtered cardiac signal having a signal frequency band.

FIG. 3 is a graph illustrating a noise signal having a noise frequency band within the signal frequency band.

FIG. 4 is a graph illustrating a noise level produced based on the noise signal.

FIG. 5 is a graph illustrating a filtered noise level.

FIG. 6 is a graph illustrating the filtered cardiac signal, a dynamic noise floor produced based on the filtered noise level, and the cardiac event detection threshold dynamically adjusted based on the dynamic noise floor.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a method and system for setting a minimum value for a dynamically adjustable detection threshold used by an implantable CRM device to detect cardiac electrical events including depolarizations from a cardiac signal. The minimum value is also dynamically adjustable based on an analysis of noise level in the cardiac signal. The CRM device senses the cardiac signal and filters the cardiac signal such that the cardiac electrical events are detected in a predetermined signal frequency band. A cardiac electrical event is detected when the amplitude of the filtered cardiac signal exceeds the dynamically adjustable detection threshold. The dynamically adjustable detection threshold is dynamically adjusted based on, for example, peak amplitudes detected from the filtered cardiac signal. A noise level in the signal frequency band is estimated by measuring the noise level in a noise frequency band. The noise frequency band is a frequency range within which the presence of signal energy is insignificant while the presence of noise energy allows for an estimation of the noise level in the signal frequency band. The estimated noise level, referred to as a dynamic noise floor, is dynamically calculated for use as the minimum value of the dynamically adjustable detection threshold. This dynamic noise floor prevents noise from being detected as cardiac electrical events.

Figure 1:
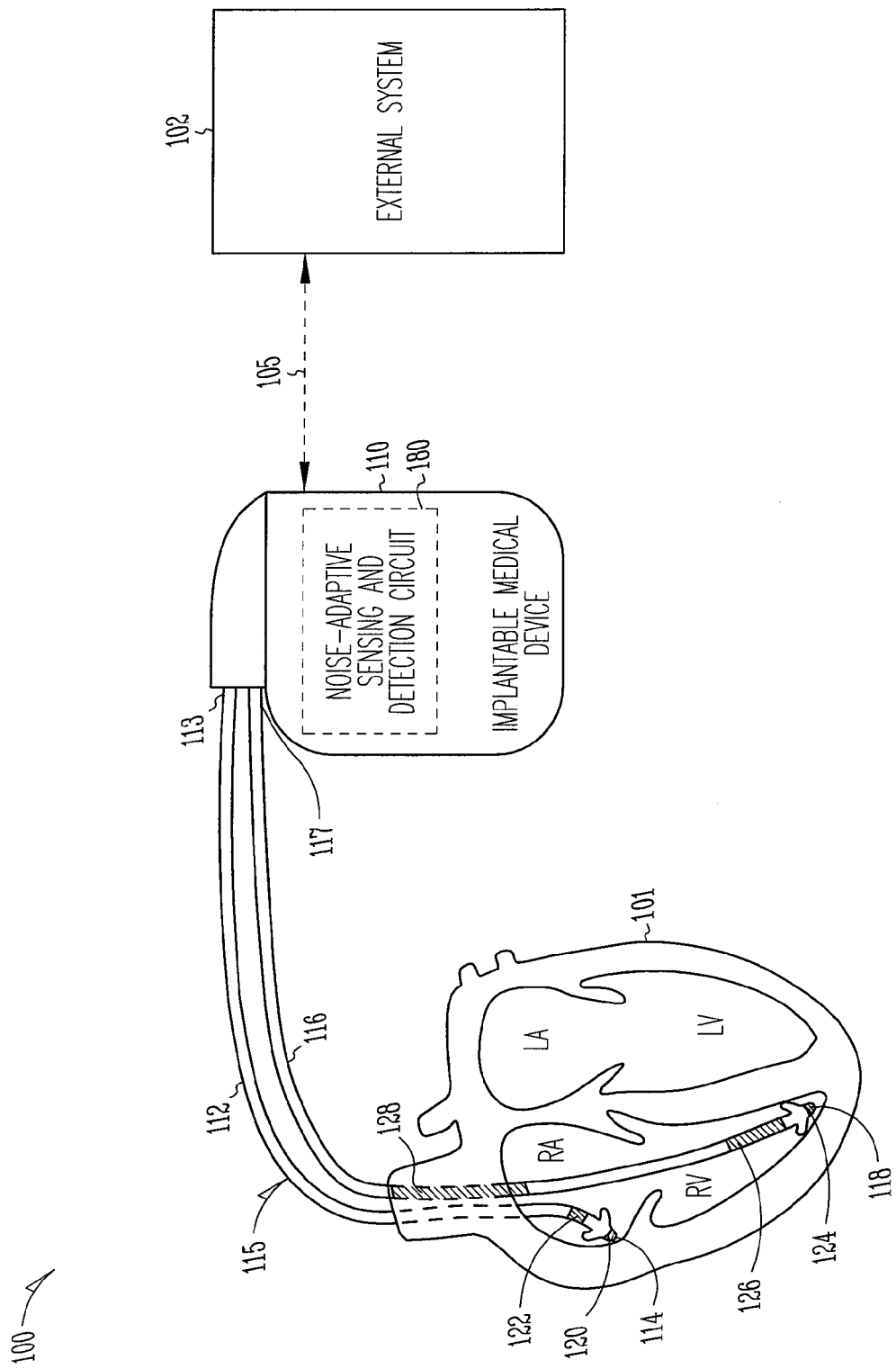
FIG. 1 is an illustration of a CRM system including an implantable medical device and portions of an environment in which the CRM system operates.

FIG. 1 is an illustration of a CRM system 100 and portions of an environment in which the CRM system 100 operates. CRM system 100 includes an implantable medical device 110 that is electrically coupled to a heart 101 through a lead system 115. An external system 102 communicates with implantable medical device 110 via a telemetry link 105.

Implantable medical device 110 includes a hermetically sealed can housing an electronic circuit. The hermetically sealed can also functions as an electrode for sensing and/or pulse delivery purposes. In one embodiment, as illustrated in FIG. 1, lead system 115 includes leads 112 and 116. Implantable medical device 110 senses cardiac signals from and delivers pacing and cardioversion/defibrillation pulses to heart 101. Lead 112 is a pacing lead that includes a proximal end 113 connected to implantable medical device 110 and a distal end 114 disposed in the right atrium (RA) of heart 101. A pacing-sensing electrode 120 is located at distal end 114. Another pacing-sensing electrode 122 is located near distal end 114. Electrodes 120 and 122 are electrically connected to implantable medical device 110 via separate conductors to allow sensing of an atrial electrogram and/or delivery of atrial pacing pulses. Lead 116 is a defibrillation lead that includes a proximal end 117 connected to implantable medical device 110 and a distal end 118 disposed in the right ventricle (RV) of heart 101. A pacing-sensing electrode 124 is located at distal end 118. A defibrillation electrode 126 is located near distal end 118 but electrically separated from pacing-sensing electrode 124. Another defibrillation electrode 128 is located at a distance from distal end 118 for supraventricular placement. Electrodes 124, 126, and 128 are electrically connected to implantable medical device 110 via separate conductors.

Electrode 124 allows sensing of a ventricular electrogram and/or delivery of ventricular pacing pulses. Electrode 126 allows delivery of cardioversion/defibrillation pulses to a ventricular region. Electrode 128 allows delivery of cardioversion/defibrillation pulses to a supraventricular region.

Implantable medical device 110 includes a noise-adaptive sensing and detection circuit 180, which includes one or more cardiac sensing systems. Each cardiac sensing system senses a cardiac signal (such as the atrial or ventricular electrogram) and detects cardiac electrical events (such as atrial or ventricular depolarizations) from each sensed cardiac signal using a dynamically adjustable detection threshold. To prevent over-sensing, the dynamically adjustable detection threshold is made noise-adaptive by providing a dynamic noise floor. The dynamic noise floor is based on a noise level dynamically estimated for the cardiac signal and provides for a minimum value for the dynamically adjustable detection threshold. Details of cardiac sensing circuit are discussed below.

External system 102 allows for programming of implantable medical device 110 and receives signals acquired by implantable medical device 110. In one embodiment, external system 102 includes a programmer. In another embodiment, external system 102 is a patient management system including an external device in proximity of implantable medical device 110, a remote device in a relatively distant location, and a telecommunication network linking the external device and the remote device. The patient management system allows access to implantable medical device 110 from a remote location, for purposes such as monitoring patient status and adjusting therapies. In one embodiment, telemetry link 105 is an inductive telemetry link. In an alternative embodiment, telemetry link 105 is a far-field radio-frequency telemetry link. Telemetry link 105 provides for data transmission from implantable medical device 110 to external system 102. This may include, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 100 (e.g., battery status and lead impedance). Telemetry link 105 also provides for data transmission from external system 102 to implantable medical device 110. This may include, for example, programming implantable medical device 110 to acquire physiological data, programming implantable medical device 110 to deliver one or more therapies.

FIGS. 2-6 are graphs illustrating a concept for a noise-adaptive cardiac event detection threshold. The graphs illustrate how the cardiac event detection threshold is established.

Figure 2:
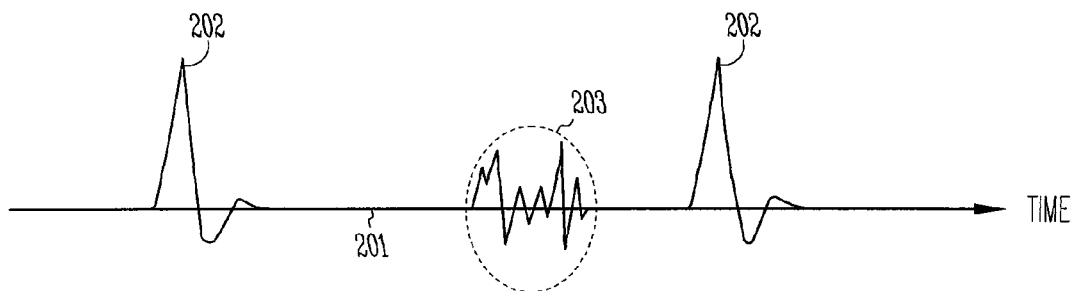
FIGS. 2-6 are graphs illustrating a concept for a cardiac event detection threshold that is noise-adaptive.

FIG. 2 is a graph illustrating a filtered cardiac signal 201. Filtered cardiac signal 201 is produced by filtering a sensed cardiac signal and has a signal frequency band. Filtered cardiac signal 201 includes cardiac electrical events 202 and a noise 203. In one embodiment, filtered cardiac signal 201 is an electrogram, and cardiac electrical events 202 are cardiac depolarizations. In one specific embodiment, filtered cardiac signal 201 is a filtered atrial electrogram, and cardiac electrical events 202 are atrial depolarizations (P-waves). In another specific embodiment, filtered cardiac signal 201 is a filtered ventricular electrogram, and cardiac electrical events 202 are ventricular depolarizations (R-waves).

Figure 3:
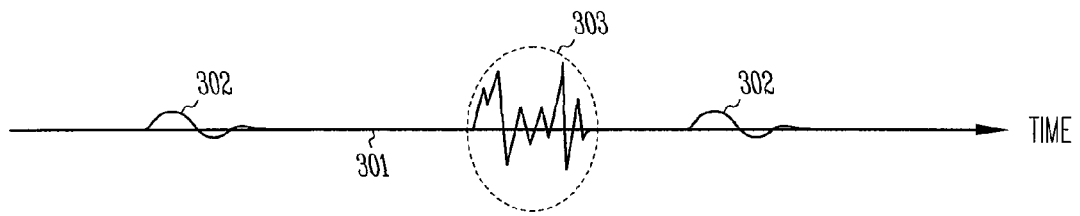

FIG. 3 is a graph illustrating a noise signal 301. Noise signal 301 is produced by filtering the same sensed cardiac signal or filtered cardiac signal 201 and has a noise frequency band. The noise frequency band is chosen to substantially suppress the cardiac electrical events while substantially retaining the noise. Noise signal 301 includes cardiac electrical events 302 and a noise 303. Cardiac electrical events 302 correspond to cardiac electrical events 202 but have substantially attenuated amplitudes. Noise 303 corresponds to noise 203 and substantially retains its characteristics.

Figure 4:
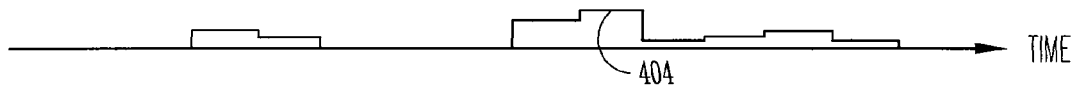

FIG. 4 is a graph illustrating a noise level 404 produced based on noise signal 301. Noise level 404 is updated periodically to indicate the amplitude or energy level of noise signal 301. In one embodiment, noise level 404 is the root-mean-square value periodically calculated from noise signal 301. In another embodiment, noise level 404 is an estimate of the root-mean-square value periodically calculated from noise signal 301. In one specific embodiment, noise level 404 is the rectified average of the amplitude of noise signal 301 calculated over successive predetermined periods. The periods are sufficiently short such that the noise level 404 is updated on a nearly continuous basis.

Figure 5:
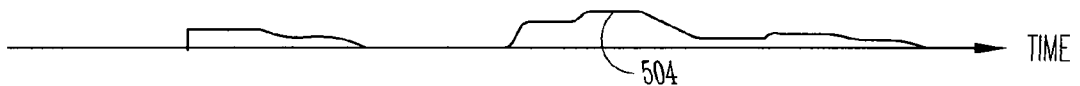

FIG. 5 is a graph illustrating a filtered noise level 504. In one embodiment, noise level 404 is smoothed by a low-pass filter to produce filtered noise level 504. In one embodiment, noise level 404 is filtered with a relative small time constant applied to rising edges and a relative large time constant applied to trailing edges.

Figure 6:
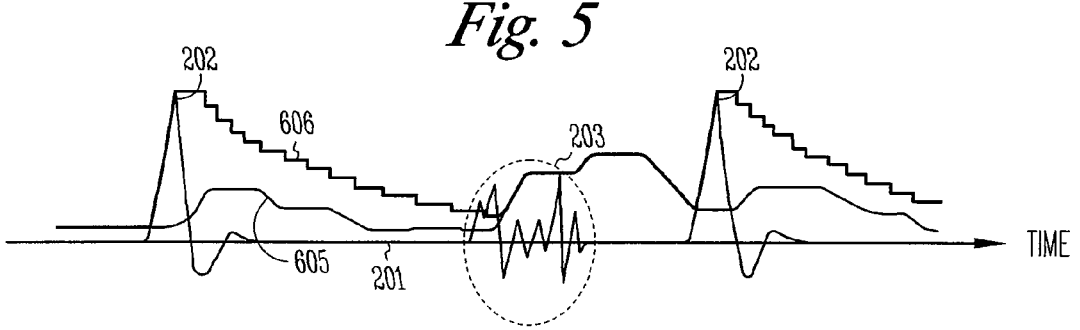

FIG. 6 is a graph illustrating filtered cardiac signal 201, a dynamic noise floor 605, and a cardiac event detection threshold 606. Dynamic noise floor 605 is produced based on filtered noise level 504. In one embodiment, dynamic noise floor 605 is produced by multiplying filtered noise level 504 with a coefficient or crest factor. In one embodiment, the coefficient is a constant empirically determined such that dynamic noise floor 605 is above a substantial majority of noise peaks anticipated in filtered cardiac signal 201. In general, the coefficient is chosen for a clinically acceptable performance in noise rejection, i.e., a clinically acceptable probability of over-sensing and/or a clinically acceptable probability of under-sensing. Cardiac event detection threshold 606 is dynamically adjusted using the dynamic noise floor as the minimum value. In one embodiment, a cardiac event detection algorithm is executed to produce a dynamically adjusted threshold. Cardiac event detection threshold 606 is set to that dynamically adjusted threshold if the dynamically adjusted threshold is higher than the dynamic noise floor and set to the dynamic noise floor if the dynamically adjusted threshold is not higher than the dynamic noise floor.

In one embodiment, as illustrated in FIG. 6, cardiac event detection threshold 606 is dynamically adjusted based on the peak amplitudes of cardiac electrical events 202 and dynamic noise floor 605. Cardiac event detection threshold 606 tracks the amplitude of filtered cardiac signal 201 when the amplitude of filtered cardiac signal 201 exceeds cardiac event detection threshold 606 until the peak amplitude of each cardiac electrical event 202 is reached. Cardiac event detection threshold 606 stays at that peak amplitude and then decays exponentially in a piecewise linear manner until a minimum detection threshold is reached. A specific example for detecting cardiac electrical events using such a dynamically adjustable detection threshold is discussed in U.S. Pat. No. 5,620,466, "DIGITAL AGC USING SEPARATE GAIN CONTROL AND THRESHOLD TEMPLATING," U.S. Pat. No. 5,658,317, "THRESHOLD TEMPLATING FOR DIGITAL AGC," and U.S. Pat. No. 5,662,688, "SLOW GAIN CONTROL," all assigned to Cardiac Pacemakers, Inc., which are hereby incorporated by reference in their entirety. Dynamic noise floor 605 provides for such a minimum detection threshold. This embodiment illustrates by way of example, but not by way of limitation, where the present subject matter is applicable. It is to be understood that, in general, the present subject matter is applicable to all CRM devices that detect cardiac electrical events using dynamically adjustable detection thresholds.

As illustrated in FIG. 6, an over-sensing event may occur at the onset of noise 203 because there is a delay in adjusting dynamic noise floor 605. That delay is due to the delay in updating noise level 404. Noise level 404 is updated at each end of the period during which the noise level is calculated from noise signal 301. A shorter period for the noise level calculation, i.e., a higher frequency for adjusting dynamic noise floor 605, further improves performance in noise rejection. Such over-sensing occurs when there is a sudden and significant increase in the noise amplitude, as illustrated in FIG. 6. An adequately determined coefficient or crest factor for producing dynamic noise floor 605 prevents over-sensing when the noise amplitude changes more gradually. It is to be understood that over-sensing is clinically problematic only when it happens too frequently. Therefore, the period for updating noise level 404 is determined such that the over-sensing associated with the delay in updating noise level 404 is limited to a degree that is clinically acceptable. In general, parameters used in producing dynamic noise floor 605, including the coefficient or crest factor for multiplying filtered noise level 504 and the period for updating noise level 404, are empirically determined, based on the nature of the noise anticipated, such that the potential degree of over-sensing and/or under-sensing are clinically acceptable.

The concept illustrated in FIGS. 2-6 is implemented by a process using digital and/or analog signal processing techniques. In one embodiment, the process is implemented using digital signal processing (DSP) technology. In another embodiment, the process includes analog signal processing. In another embodiment, the process includes combined analog and digital signal processing. For example, dynamic noise floor 605 is produced from noise signal 301 using DSP, while the rest of the process is implemented by analog circuitry. Generally, DSP requires the smallest circuit size and power consumption, which are important factors to consider in the design of any battery-powered implantable medical device.

In one specific embodiment, the cardiac signal is digitized at approximately 400 samples per second before filtered cardiac signal 201 and noise signal 301 are produced. The signal frequency band is approximately 10-100 Hz. The noise frequency band is approximately 50-100 Hz. Noise level 404 is calculated based on noise signal 301 about every 160 milliseconds (or 64 samples of noise signal). Filtered noise level 504 is produced by filtering noise level 404 with a finite impulse response (FIR) filter.

Figure 7:
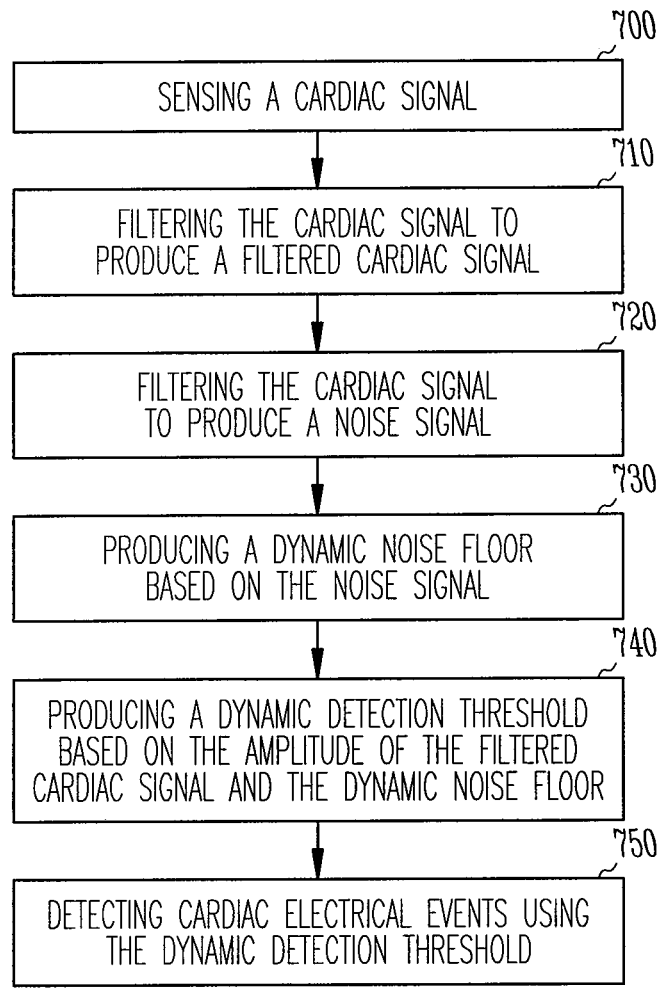
FIG. 7 is a flow chart illustrating a method for cardiac sensing and event detection using the cardiac event detection threshold.

FIG. 7 is a flow chart illustrating a method for cardiac sensing and event detection using a dynamically adjustable cardiac event detection threshold such as cardiac event detection threshold 606 illustrated in FIG. 6. The method is discussed in detail below using digital signal processing as an example of implementation. However, those skilled in the art will understand, upon reading and comprehending this document, that the method can also be implemented using analog signal processing or combined analog and digital signal processing.

A cardiac signal is sensed at 700. Examples of the cardiac signal includes atrial and ventricular electrograms. The cardiac signal is digitized by sampling at a predetermined sampling frequency. In one embodiment, the sampling frequency is in a range between 200 and 1,000 samples per second. In one specific embodiment, the sampling frequency is approximately 400 samples per second. Before being digitized, the cardiac signal is filtered with an analog low-pass filter having a cutoff frequency that is one half of the sampling frequency or lower.

The cardiac signal is filtered to produce a filtered cardiac signal at 710. The filtered cardiac signal provides for detection the cardiac electrical events in a signal frequency band. In one embodiment, in which the cardiac signal is an electrogram, the signal frequency band has a low cutoff frequency in a range between 1 Hz and 20 Hz and a high cutoff frequency in a range between 50 Hz and 200 Hz.

The cardiac signal is also filtered to produce a noise signal at 720. The noise signal provides for measurement of a noise level in a noise frequency band. In one embodiment, the noise frequency band is within the signal frequency band and is substantially narrower than the signal frequency band. The noise frequency band is chosen to allow an estimation of noise energy across the signal frequency band. In one embodiment, the cardiac signal is directly filtered to produce the noise signal. In another embodiment, the filtered cardiac signal having the signal frequency band is filtered again to produce the noise signal. In one embodiment, in which the cardiac signal is an electrogram, the noise frequency band has a low cutoff frequency in a range between 40 Hz and 60 Hz and a high cutoff frequency in a range between 70 Hz and 200 Hz. It is generally observed that in an electrogram having a signal frequency band of approximately 10-100 Hz, the signal energy is concentrated in the lower one half of the band while noise are typically evenly distributed throughout the band. Thus, in one embodiment, the noise frequency band is chosen to be equal to approximately the upper one half of the signal frequency band.

A dynamic noise floor is produced based on the noise signal at 730. The noise signal is a digitized signal including noise samples each having a noise sample amplitude. In one embodiment, each noise sample amplitude is set to a maximum amplitude if it exceeds that maximum amplitude. This avoids inclusion of large spurious deflections in the noise signal in the process that produces the dynamic noise floor. The maximum amplitude is dynamically determined based on the present dynamic noise floor. In one specific embodiment, the maximum amplitude equals eight times the present dynamic noise floor. Then, a noise level is determined based on the noise sample amplitudes of a predetermined number of successive noise samples. In one specific embodiment, the noise level is an average calculated over every 64 successive noise samples. With the sampling frequency of 400 samples per second, this updates the noise level every 160 milliseconds. In one embodiment, the noise level is a root-mean-square value calculated for the noise sample amplitudes of the predetermined number of successive noise samples. In another embodiment, the noise level is an estimate of a root-mean-square value calculated for the noise sample amplitudes of the predetermined number of successive noise samples. In a specific embodiment, the noise sample amplitudes are rectified, and the noise level is an average of the rectified noise sample amplitudes calculated for the noise sample amplitudes of the predetermined number of successive noise samples. Such a rectified average provides a reasonable estimation of the root-mean-square value for the purpose of producing the dynamic noise floor. In one embodiment, the noise level is filtered with a low-pass filter such as an FIR filter. The filtered noise level is multiplied by a predetermined coefficient to produce the dynamic noise floor. The coefficient is empirically determined based on a desirable performance in noise rejection. The probability of over-sensing (detecting a noise as a cardiac electrical event) is balanced against the probability of under-sensing (failing to detect a cardiac electrical event). For example, when cardiac electrical events are detected for controlling an anti-tachyarrhythmia therapy, the coefficient is experimentally determined to minimize the probability of over-sensing after first minimizing the probability of under-sensing.

A dynamic detection threshold based on the amplitude of the filtered cardiac signal and the dynamic noise floor at 740. An initial detection threshold is produced based on at least the amplitude of the filtered cardiac signal. In one embodiment, peak amplitudes associated with cardiac electrical events in the filtered cardiac signal are detected. The initial detection threshold is produced based on at least the peak amplitudes. An specific example of producing such an initial detection threshold is discussed in U.S. Pat. Nos. 5,620,466, 5,658,317, and 5,662,688, as cited above. The dynamic detection threshold is set to the initial detection threshold when the initial detection threshold is higher than the dynamic noise floor and to the dynamic noise floor when the initial detection threshold is not higher than the dynamic noise floor.

The cardiac electrical events are detected using the dynamic detection threshold at 750. The detection of each cardiac electrical event is indicated when the amplitude of the cardiac signal exceeds the dynamic detection threshold. In one embodiment, in which the cardiac signal is an electrogram, the cardiac electrical events include atrial depolarizations (P-waves) and/or ventricular depolarizations (R-waves).

In one embodiment, the detection of cardiac electrical events is performed for controlling a delivery of a cardiac therapy. In one specific embodiment, a delivery of an anti-bradyarrhythmia therapy is controlled based on the outcome of detecting the cardiac electrical events using the method discussed above with reference to FIG. 7. In another specific embodiment, a delivery of an anti-tachyarrhythmia therapy is controlled based on the outcome of detecting the cardiac electrical events using the method discussed above with reference to FIG. 7. In another specific embodiment, deliveries of anti-bradyarrhythmia and anti-tachyarrhythmia therapies are concurrently controlled based on the outcome of detecting the cardiac electrical events using the method discussed above with reference to FIG. 7.

In one embodiment, in addition to detecting the cardiac electrical events, a measure of noise presence in the cardiac signal, such as a signal-to-noise ratio (SNR), is calculated to serve as one parameter used for controlling the delivery of the cardiac therapy. In one embodiment, a running average of the peak amplitudes associated with cardiac electrical events in the cardiac signal is calculated. An SNR is dynamically calculated as the ratio of the running average of the peak amplitudes to the dynamic noise floor. In a further embodiment, a low SNR is indicated when the SNR is lower than a predetermined threshold SNR. The low SNR serves as an alert signal for a particularly noisy cardiac signal. In another further embodiment, a persistently low SNR when the SNR is lower than the predetermined threshold SNR for a predetermined period of time or a predetermined number of heart beats.

Figure 8:
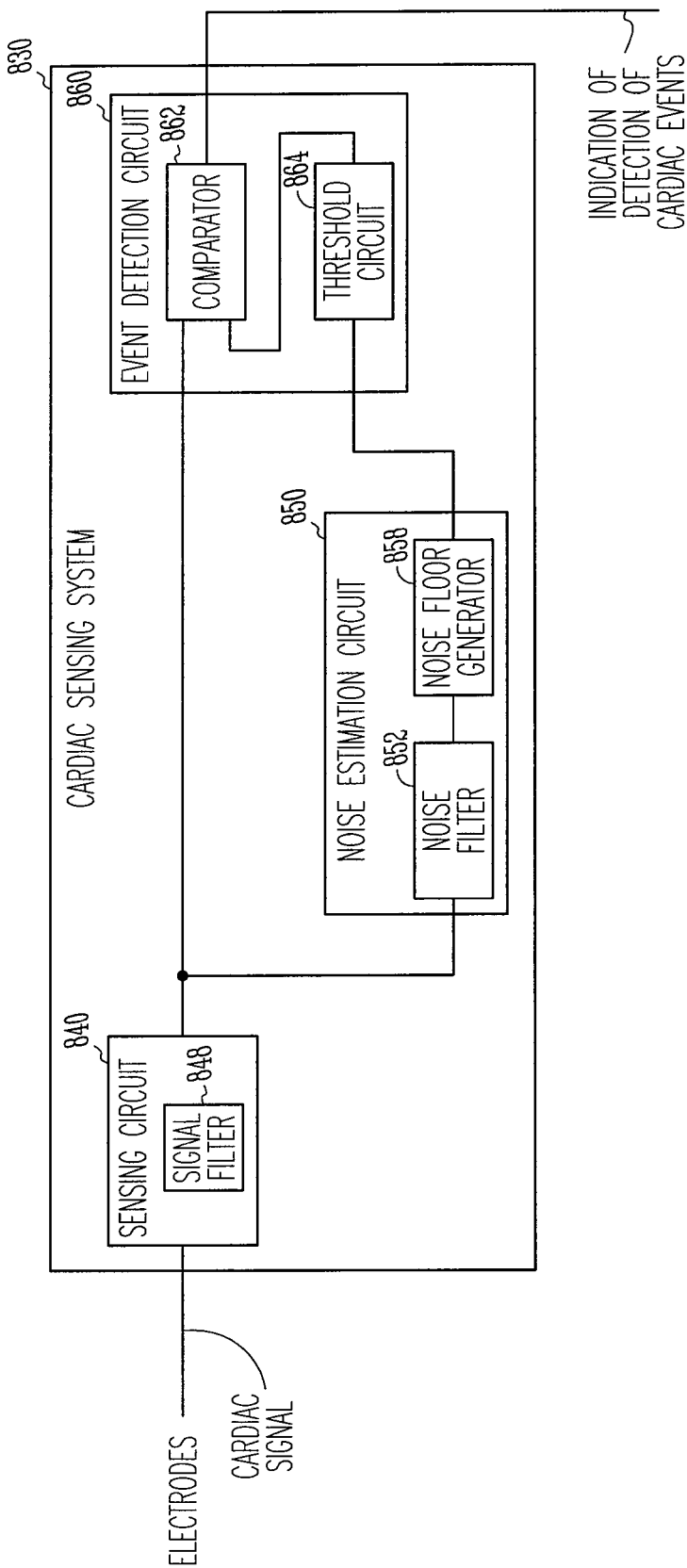
FIG. 8 is a block diagram illustrating an embodiment of a cardiac sensing system.

FIG. 8 is a block diagram illustrating an embodiment of a cardiac sensing system 830. Cardiac sensing system 830 is one embodiment of the cardiac sensing system of noise-adaptive sensing and detection circuit 180 and includes a sensing circuit 840, a noise estimation circuit 850, and an event detection circuit 860. In one embodiment, noise-adaptive sensing and detection circuit 180 includes a plurality of cardiac sensing channels each including a circuit of cardiac sensing system 830 as illustrated in FIG. 8.

Sensing circuit 840 senses a cardiac signal such as an electrogram. Sensing circuit 840 receives the cardiac signal from electrodes placed in or on the heart and includes a signal filter 848 to filter the cardiac signal. Signal filter 848 produces a filtered cardiac signal having a signal frequency band.

Noise estimation circuit 850 includes a noise filter 852 and a noise floor generator 858. Noise filter 852 produces a noise signal based on the cardiac signal. The noise signal has a noise frequency band that is substantially different from the signal frequency band. Noise floor generator 858 produces a dynamic noise floor based on the noise signal.

Event detector 860 includes a comparator 862 and a threshold circuit 864. Comparator 862 has a first input to receive the filtered cardiac signal, a second input to receive a detection threshold, and an output to indicate a detection of a cardiac electrical event when the signal amplitude exceeds the detection threshold. Threshold circuit 864 dynamically produces the detection threshold based on at least the filtered cardiac signal and the dynamic noise floor.

In one embodiment, cardiac sensing system 830 is a substantially analog circuit. In another embodiment, cardiac sensing system 830 is a substantially digital circuit. In one specific embodiment, sensing circuit 840 digitizes the cardiac signal before feeding it to signal filter 848 and noise filter 852. This allows signal filter 848, noise estimation circuit 850, and event detection circuit 860 to be implemented by DSP technology.

Figure 9:
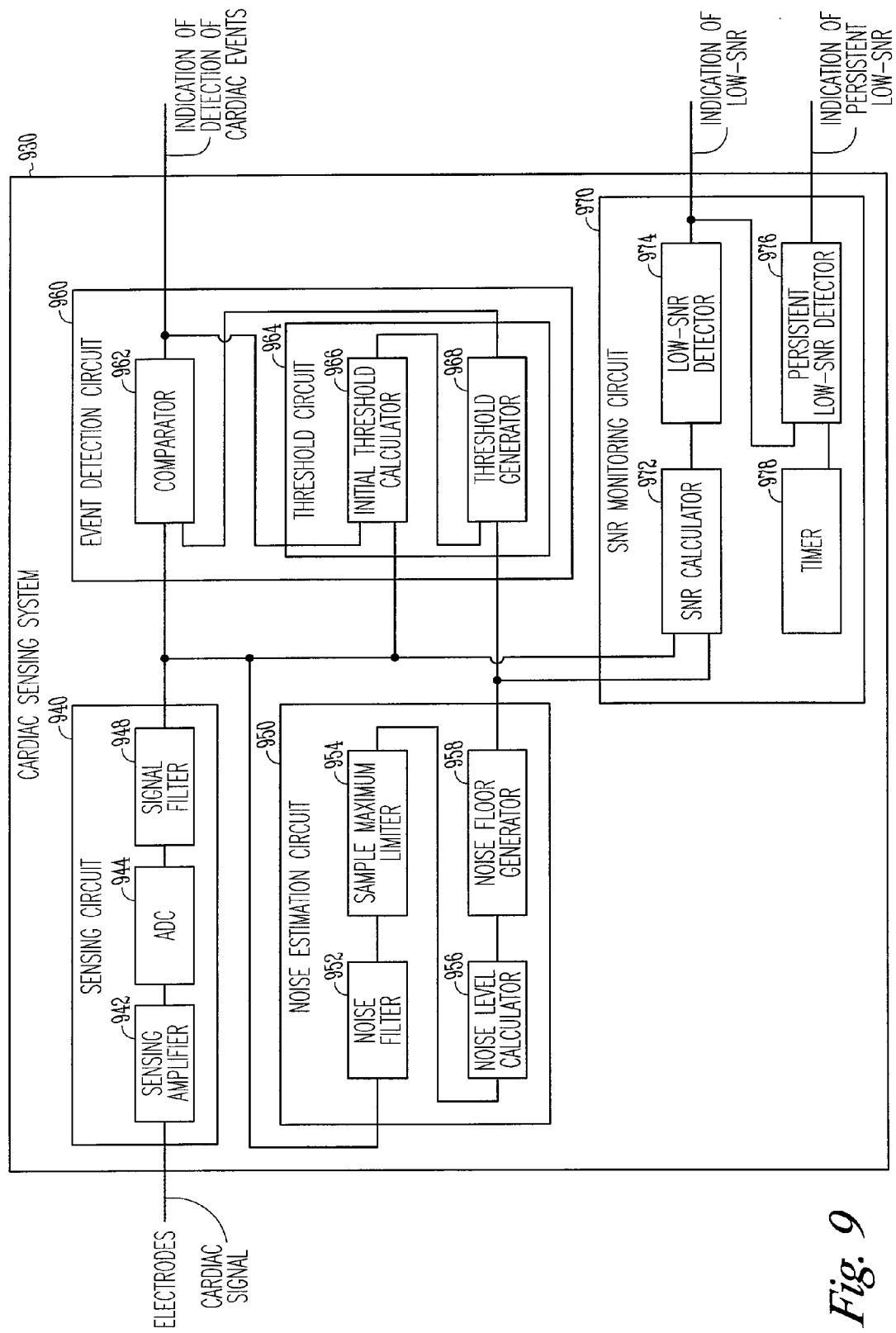
FIG. 9 is a block diagram illustrating a specific embodiment of the cardiac sensing system.

FIG. 9 is a block diagram illustrating a cardiac sensing system 930, which is a specific embodiment of cardiac sensing system 830. Cardiac sensing system 930 includes a sensing circuit 940, a noise estimation circuit 950, an event detection circuit 960, and an SNR monitoring circuit 970. As illustrated in FIG. 9, cardiac sensing system 930 is implemented using substantially digital circuitry. However, those skilled in the art will understand, upon reading and comprehending this document, that cardiac sensing system 930 can also be implemented using substantially analog circuitry or combined analog and digital circuitry.

As a specific embodiment of sensing circuit 840, sensing circuit 940 senses a cardiac signal and includes a sensing amplifier 942, an analog-to-digital converter (ADC) 944, and a signal filter 948. Sensing amplifier 942 receives the cardiac signal through electrodes such as intracardiac or epicardial electrodes and amplifies the cardiac signal. In one embodiment, sensing amplifier 942 also includes an analog band-pass filter to filter the cardiac signal before its digitization. ADC 944 digitizes the cardiac signal by sampling it at a predetermined sampling frequency. In one embodiment, the sampling frequency is in the range between 200 and 1,000 samples per second. In one specific example, the sample rate is approximately 400 samples per second. Signal filter 948 produces a filtered cardiac signal by filtering the digitized cardiac signal. Signal filter 948 is a band-pass filter having a low cutoff frequency and a high cutoff frequency. In one embodiment, signal filter 948 has a low cutoff frequency in a range between 1 Hz and 20 Hz and a high cutoff frequency in a range between 50 Hz and 200 Hz. In one specific embodiment, in which the cardiac signal is an electrogram, signal filter 948 has a low cutoff frequency of approximately 10 Hz and a high cutoff frequency of approximately 100 Hz. The filtered cardiac signal has a signal frequency band dependent on the cutoff frequencies of signal filter 948.

Noise estimation circuit 950 is a specific embodiment of noise estimation circuit 850 and includes a noise filter 952, a sample maximum limiter 954, a noise level calculator 956, and a noise floor generator 958. Noise filter 952 produces a noise signal having a noise frequency. In one embodiment, the noise frequency band is within the signal frequency band and substantially narrower than the signal frequency band. In one embodiment, as illustrated in FIG. 9, noise filter 952 is a high-pass filter that receives the filtered cardiac signal and produces the noise signal by further filtering the filtered cardiac signal. In one embodiment, noise filter 952 (high-pass filter) has a cutoff frequency in a range between 40 Hz and 60 Hz. In one specific embodiment, in which the cardiac signal is an electrogram and signal filter 948 has a low cutoff frequency of approximately 10 Hz and a high cutoff frequency of approximately 100 Hz, noise filter 952 (high-pass filter) has a cutoff frequency of approximately 50 Hz. In an alternative embodiment, noise filter 952 is a band-pass filter that receives the digitized cardiac signal and produces the noise signal by filtering the digitized cardiac signal. In one embodiment, noise filter 952 (band-pass filter) has a low cutoff frequency in a range between 40 Hz and 60 Hz and a high cutoff frequency in a range between 50 Hz and 200 Hz. In one specific embodiment, in which the cardiac signal is an electrogram and signal filter 948 has a low cutoff frequency of approximately 10 Hz and a high cutoff frequency of approximately 100 Hz, noise filter 952 (band-pass filter) has a low cutoff frequency of approximately 50 Hz and a high cutoff frequency of approximately 100 Hz. The noise signal is a digitized signal including noise samples each having a noise sample amplitude.

Sample maximum limiter 954 sets each noise sample amplitude to a maximum amplitude if that noise sample amplitudes exceeds the maximum amplitude. In one embodiment, sample maximum limiter 954 includes a maximum amplitude calculator to dynamically calculate the maximum amplitude based on the dynamic noise floor. In one specific embodiment, the maximum amplitude calculator dynamically sets the maximum amplitude to eight times the dynamic noise floor.

Noise level calculator 956 calculates a noise level based on the noise amplitudes of a predetermined number of successive noise samples. In one embodiment, in which ADC 944 digitizes the cardiac signal at the sampling frequency of 400 samples per second, noise level calculator 956 calculates the noise level based on the noise sample amplitudes of 64 successive noise samples. That is, noise level calculator 956 calculates the noise level based on the noise sample amplitudes measured over 160 milliseconds (64 samples/400 samples per second). In one embodiment, the noise level is the root-mean-square value for the noise sample amplitudes of the predetermined number of successive noise samples. Noise level calculator 956 includes a root-mean-square value calculator to calculate the noise level. In another embodiment, the noise level is an estimate of the root-mean-square value for the noise sample amplitudes of the predetermined number of successive noise samples. This provides a way to reduce circuit size and power consumption associated to the computation of the root-mean-square value. Noise level calculator 956 includes a root-mean-square value estimator to calculate the noise level. In one specific embodiment, a rectified average is calculated as the estimate of the root-mean-square value. Noise level calculator 956 includes a rectifier and an average calculator. The rectifier rectifies the noise sample amplitudes. The average calculator calculates the average of the rectified noise sample amplitudes for the noise sample amplitudes of the predetermined number of successive noise samples.

Noise floor generator 958 generates the dynamic noise floor based on the calculated noise level. The noise floor is an estimate of the noise level in the signal frequency band calculated based on the noise level calculated for the noise frequency band. In one embodiment, noise floor generator 958 includes a low-pass filter to smooth the calculated noise level and a noise level converter to produce the dynamic noise floor by converting the noise level for the noise frequency band to an estimate of the noise level for the signal frequency band. In one specific embodiment, the low-pass filter includes an FIR filter, and the noise level converter produces the dynamic noise floor by multiplying the filtered noise level with a predetermined coefficient. The coefficient is empirically determined and programmed into cardiac sensing system 930.

Event detector 960 is a specific embodiment of event detection circuit 860 and includes a comparator 962 and a threshold circuit 964. Comparator 962 has a first input to receive the filtered cardiac signal, a second input to receive a detection threshold, and an output to indicate a detection of a cardiac electrical event when the amplitude of the filtered cardiac signal exceeds the detection threshold. Threshold circuit 964 includes an initial threshold calculator 966 and a threshold generator 968. Initial threshold calculator 966 produces an initial detection threshold based on at least the amplitude of the filtered cardiac signal and the dynamic noise floor. In one embodiment, initial threshold calculator 966 includes a peak measurement circuit that measures peak amplitudes from the filtered cardiac signal. The peak amplitudes are each an amplitude measured at the peak of a detected cardiac electrical event. Initial threshold calculator 966 sets the initial detection threshold based on at least the peak amplitudes. One example of setting a cardiac event detection threshold based on peak amplitudes of a cardiac signal is discussed in U.S. Pat. Nos. 5,620,466, 5,658,317, and 5,662,688, as cited above. Threshold generator 968 sets the detection threshold to the initial detection threshold when the initial detection threshold is higher than the dynamic noise floor, and to the dynamic noise floor when the initial detection threshold is not higher than the dynamic noise floor.

SNR measurement circuit 970 includes an SNR calculator 972, a low-SNR detector 974, a persistent low-SNR detector 976, and a timer 978. SNR calculator 972 dynamically calculates an SNR indicative of the degree of presence of noise in the cardiac signal. In one embodiment, SNR calculator 972 includes a signal amplitude average calculator to calculate a running average of the peak amplitudes measured from the filtered cardiac signal. SNR calculator 972 dynamically calculates the SNR as the ratio of the running average of the peak amplitudes to the dynamic noise floor. Low-SNR detector 974 includes an SNR comparator having a first input to receive the SNR, a second input to receive a predetermined threshold SNR, and an output to indicate a low SNR when the SNR is lower than the predetermined threshold SNR. After a low SNR is detected, persistent low-SNR detector 976 detects a persistently low SNR. In one embodiment, timer 978 starts timing in response to an indication of the low SNR. If the output of low-SNR detector 974 indicates the low SNR for at least a predetermined period of time as timed by timer 978, persistent low-SNR detector 976 indicates a detection of persistently low SNR. In one specific embodiment, timer 978 includes a counter. The counter starts counting heart beats in response to an indication of the low SNR. If the output of low-SNR detector 974 indicates the low SNR for at least a predetermined number of heart beats as counted by the counter, persistent low-SNR detector 976 indicates a detection of persistently low SNR.

Figure 10:
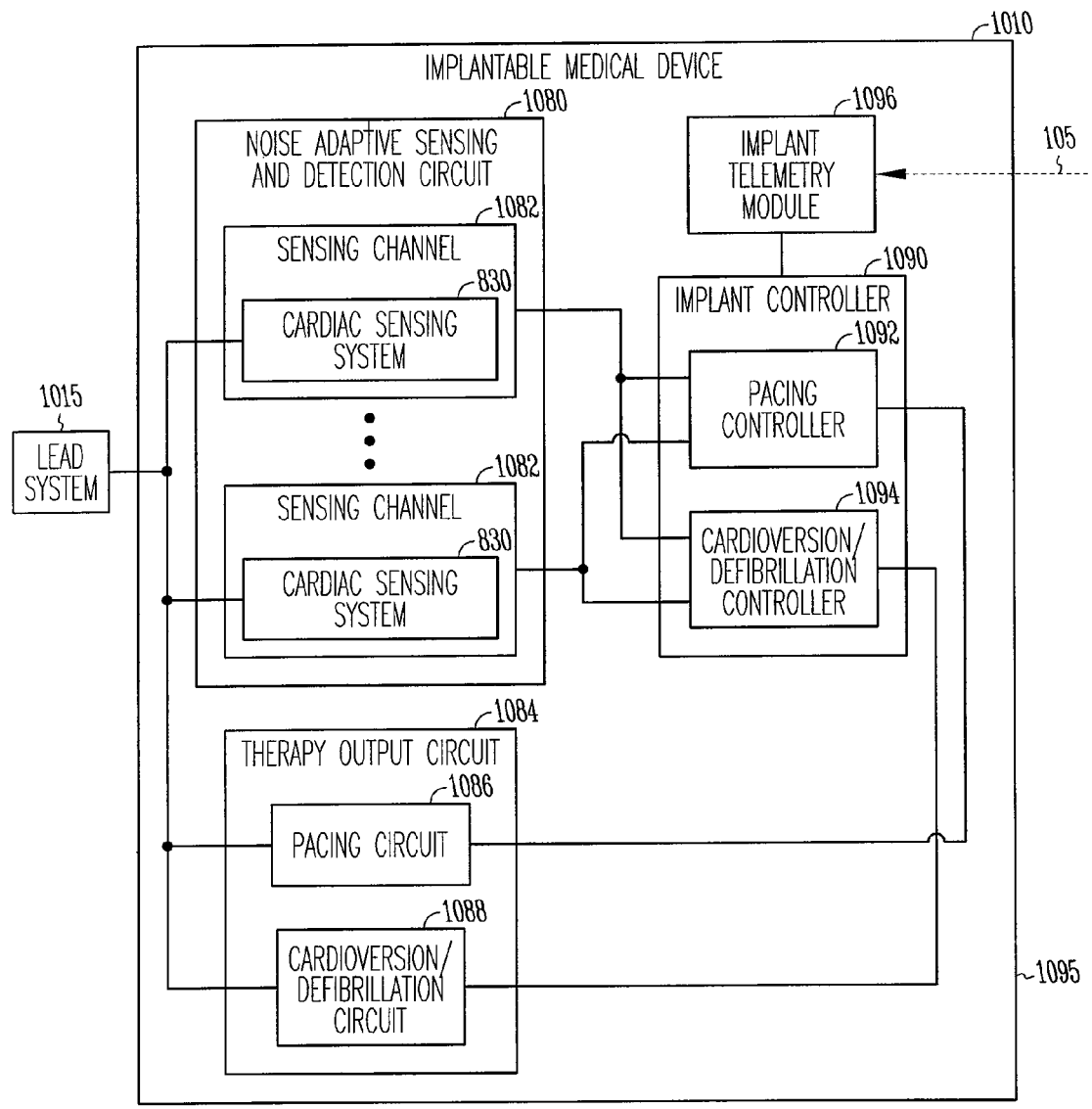
FIG. 10 is a block diagram illustrating an embodiment of portions of a circuit of the implantable medical device including the cardiac sensing system.

FIG. 10 is a block diagram illustrating an embodiment of portions of a circuit of an implantable medical device 1010. As an exemplary embodiment of implantable medical device 110 discussed for illustrative but not restrictive purposes, implantable medical device 1010 is an implantable cardioverter/defibrillator (ICD) with cardiac pacing capabilities, i.e., a combined pacemaker and cardioverter/defibrillator.

Implantable medical device 1010 includes hermetically sealed can 1095 that houses a circuit including a noise-adaptive sensing and detection circuit 1080, a therapy output circuit 1084, an implant controller 1090, and an implant telemetry module 1096. The circuit is powered by a battery that is also housed in can 1095. Implant telemetry module 1096 provides implantable medical device 1010 with the capability of communicating with an external device or system such as external system 102 via telemetry link 105.

Noise-Adaptive sensing and detection circuit 1080 is one embodiment of noise-adaptive sensing and detection circuit 180 and includes one or more sensing channels 1082 each including cardiac sensing system 830 (or 930 as a specific embodiment). Each sensing channel 1082 is used to sense one electrogram from the heart and detect depolarizations form the sensed electrogram. Therapy output circuit 1084 includes a pacing circuit 1086 to deliver pacing pulses to the heart and a cardioversion/defibrillation circuit 1088 to deliver cardioversion/defibrillation pulses to the heart. Noise-Adaptive sensing and detection circuit 1080 and therapy output circuit 1084 are electrically coupled to the heart through a lead system 1015. Lead system 1015 includes a plurality of electrodes placed in and/or on the heart. One example of lead system 1015 is lead system 115.

Implant control circuit 1090 includes a pacing controller 1092 and a cardioversion/defibrillation 1094. Pacing controller 1092 controls the delivery of the pacing pulses, and cardioversion/defibrillation controller 1094 controls the delivery of the cardioversion/defibrillation pulses, based on the detected cardiac depolarizations. Cardiac sensing system 830 allows the cardiac depolarizations to be detected using the same detection circuit configuration for use in the control of both pacing and cardioversion/defibrillation deliveries. In other words, sensing channels 1082 are a plurality of substantially identical circuits even though one or more channels detect depolarizations for pacing controller 1092 and another one or more channels detect depolarizations for cardioversion/defibrillation 1094.

Noise in a cardiac signal such as an electrogram potentially causes different problems in anti-bradyarrhythmia therapy and anti-tachyarrhythmia therapy. One example is that myoelectric signals associated with diaphragmatic contractions may be sensed by a cardiac sensing circuit. If the diaphragm contractions are detected as cardiac depolarizations, anti-bradyarrhythmia pacing may be erroneously inhibited, causing dizziness in the patient, or a defibrillation pulse may be erroneously delivered, causing unnecessary pain in the patient and shortening an ICD's life expectancy. Because such diaphragm contractions may have amplitudes similar to that of cardiac depolarizations when seen in an electrogram, increasing the detection threshold may cause under-sensing. Such under-sensing may cause unsynchronized pacing that reduces the effectiveness of anti-bradyarrhythmia pacing and/or erroneous inhibition of the delivery of a defibrillation pulse, which is life-threatening. Because the presence of noise in an electrogram is expected, different detection strategies have been applied to detect cardiac depolarization depending on the purpose, i.e., whether the cardiac depolarizations are detected for controlling pacing or cardioversion/defibrillation. To ensure patient safety, a known strategy is to set the detection threshold with a bias toward under-sensing for control of anti-bradyarrhythmia pacing and to set the detection threshold to with a bias toward over-sensing for control of cardioversion/defibrillation. However, this not only requires different circuits and/or different programming procedures, but also causes sub-optimal pacing therapy and/or unnecessary delivery of cardioversion/defibrillation energy.

Because the noise is the cause of the problem, and the level of noise presence in a cardiac signal changes over time, using the dynamic noise floor as discussed in this document provides for a performance in cardiac electrical event detection that is relatively independent of the noise. The use of the dynamic noise floor also provides for a circuit configuration that is suitable for detecting cardiac electrical events in both pacing and cardioversion/defibrillation therapies. In one embodiment, cardiac sensing system 830 is used as the basic circuit configuration for detection of cardiac electrical events for both anti-bradyarrhythmia pacing control and cardioversion/defibrillation control purposes.

While the present subject matter is described above using its application in an implantable CRM device as an example, it is to be understood that it is generally applicable in implantable or non-implantable, cardiac or non-cardiac medical devices and systems. The present subject matter provides for a method and system for setting a dynamic minimum value for a dynamically adjustable detection threshold used to detect events from a signal sensed by a medical device to indicate biological activities. The medical device senses the signal and filters the signal such that the events are detected in a predetermined signal frequency band. An event is detected when the amplitude of the signal exceeds the dynamically adjustable detection threshold. The noise level in the signal frequency band is estimated by measuring the noise energy in a noise frequency band. The noise frequency band is selected from a frequency range within which the presence of signal energy is insignificant while the noise level can be measured to serve as the basis for estimating the noise level in the signal frequency band. This dynamically estimated noise level is used as the minimum value for the dynamically adjustable detection threshold to prevent noise from being detected as the events.

It is to be understood that the above detailed description is intended to be illustrative, and not restrictive. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
   a sensing circuit adapted to sense a cardiac signal, the sensing circuit including a signal filter adapted to produce a filtered cardiac signal having a signal frequency band by filtering the sensed cardiac signal;
   a noise estimation circuit coupled to the sensing circuit, the noise estimation circuit adapted to dynamically generate a noise floor using a noise signal having a noise frequency band, the noise floor being an estimate of noise level in the signal frequency band, the noise estimation circuit including a noise filter adapted to produce the noise signal having the noise frequency band by filtering the sensed cardiac signal, the noise frequency band being substantially different from the signal frequency band; and
   an event detection circuit coupled to the sensing circuit and the noise estimation circuit, the event detection circuit adapted to dynamically adjust a detection threshold using at least the filtered cardiac signal and the noise floor and to detect cardiac electrical events using the filtered cardiac signal and the detection threshold, the noise floor used as a minimum value of the detection threshold.

2. The device of claim 1, wherein the event detection circuit comprises a threshold circuit including:
   an initial threshold calculator adapted to produce an initial detection threshold using at least the filtered cardiac signal; and
   a threshold generator adapted to set the detection threshold to the initial detection threshold when the initial detection threshold is higher than the noise floor and to the noise floor when the initial detection threshold is not higher than the dynamic noise floor.

3. An implantable medical device, comprising:
   a sensing circuit adapted to sense a cardiac signal, the sensing circuit including a signal filter adapted to produce a filtered cardiac signal having a signal frequency band by filtering the sensed cardiac signal;
   a noise estimation circuit coupled to the sensing circuit, the noise estimation circuit adapted to dynamically generate a noise floor using a noise signal having a noise frequency band, the noise floor being an estimate of noise level in the signal frequency band, the noise estimation circuit including a noise filter adapted to produce the noise signal by filtering the sensed cardiac signal or the filtered cardiac signal, the noise frequency band allowing for estimation of noise energy across the signal frequency band; and
   an event detection circuit coupled to the sensing circuit and the noise estimation circuit, the event detection circuit adapted to dynamically adjust a detection threshold using at least the filtered cardiac signal and the noise floor and to detect cardiac electrical events using the filtered cardiac signal and the detection threshold, the noise floor used as a minimum value of the detection threshold.

4. The device of claim 3, wherein the noise filter is adapted to produce the noise signal using the filtered cardiac signal, and the noise frequency band is within and substantially narrower than the signal frequency band.

5. The device of claim 3, wherein the noise estimation circuit comprises:
   a noise level calculator adapted to calculate a noise level for the noise frequency band using the noise signal; and
   a noise floor generator adapted to generate the noise floor using the noise level calculated for the noise frequency band.

6. The device of claim 5, wherein the sensing circuit comprises an analog-to-digital converter adapted to digitize the cardiac signal, the signal filter comprises a digital signal filter, and the noise filter comprises a digital noise filter adapted to produce the noise signal being a digital signal including noise samples each having a noise sample amplitude, and wherein the noise level calculator is adapted to calculate the noise level using the noise sample amplitudes of successive samples of the noise samples.

7. The device of claim 6, wherein the noise estimation circuit comprises a sample maximum limiter coupled between the noise filter and the noise level calculator, the sample maximum limiter adapted to set each of the noise sample amplitude to a maximum amplitude if the each of the noise sample amplitudes exceeds the maximum amplitude.

8. The device of claim 7, wherein the noise floor generator comprises:
   a low-pass filter adapted to filter the calculated noise level; and
   a noise level converter adapted to produce the noise floor by multiplying the filtered noise level with a coefficient.

9. The device of claim 3, wherein the signal filter comprises a band-pass filter, and the noise filter comprises a high-pass filter configured to receive the filtered cardiac signal and to produce the noise signal by further filtering the filtered cardiac signal.

10. The device of claim 9, wherein the band-pass filter has a first low cutoff frequency in a range between 1 Hz and 20 Hz and a first high cutoff frequency in a range between 50 Hz and 200 Hz, and the high-pass filter has a second low cutoff frequency in a range between 40 Hz and 60 Hz.

11. The device of claim 10, wherein the first low cutoff frequency is approximately 10 Hz, the first high cutoff frequency is approximately 100 Hz, and the second low cutoff frequency is approximately 50 Hz.

12. The device of claim 3, wherein the signal filter comprises a signal frequency band-pass filter, and the noise filter comprises a noise frequency band-pass filter configured to receive the cardiac signal and to produce the noise signal by filtering the cardiac signal.

13. The device of claim 12, wherein the signal frequency band-pass filter has a first low cutoff frequency in a range between 1 Hz and 20 Hz and a first high cutoff frequency in a range between 50 Hz and 200 Hz, and the noise frequency band-pass filter has a second low cutoff frequency in a range between 40 Hz and 60 Hz and a second high cutoff frequency in a range between 50 Hz and 200 Hz.

14. The device of claim 13, wherein the first low cutoff frequency is approximately 10 Hz, the first high cutoff frequency is approximately 100 Hz, and the second low cutoff frequency is approximately 50 Hz, the second high cutoff frequency is approximately 100 Hz.

15. An implantable medical device, comprising:
   a sensing circuit adapted to sense a cardiac signal, the sensing circuit including a signal filter adapted to produce a filtered cardiac signal having a signal frequency band by filtering the sensed cardiac signal;
   a noise estimation circuit coupled to the sensing circuit, the noise estimation circuit adapted to dynamically generate a noise floor using a noise signal, the noise floor being an estimate of noise level in the signal frequency band, the noise estimation circuit including a noise filter adapted to produce the noise signal by filtering the filtered cardiac signal, the noise signal having a noise frequency band that is substantially different from the signal frequency band;
   an event detection circuit coupled to the sensing circuit and the noise estimation circuit, the event detection circuit adapted to dynamically adjust a detection threshold using at least the filtered cardiac signal and the noise floor and to detect cardiac electrical events using the filtered cardiac signal and the detection threshold, the noise floor used as a minimum value of the detection threshold;
   a peak measurement circuit adapted to measure peak amplitudes of the filtered cardiac signal; and
   a low signal-to-noise ratio (SNR) detection circuit adapted to calculate a running average of the peak amplitudes, calculate a dynamic SNR being a ratio of the running average of the peak amplitudes to the noise floor, and indicate a low SNR when the dynamic SNR is lower than a threshold SNR.

16. The device of claim 15, comprising:
   a timer adapted to start a predetermined period in response to an indication of the low SNR, the predetermined period measured by time or number of heart beats; and
   a persistent low-SNR detector adapted to indicate a persistently low SNR in response to the low SNR being indicated for the predetermined period.

17. An implantable medical device, comprising:
a sensing circuit adapted to sense a cardiac signal; the sensing circuit including a signal filter adapted to produce a filtered cardiac signal having a signal frequency band by filtering the sensed cardiac signal;
a noise estimation circuit coupled to the sensing circuit, the noise estimation circuit adapted to dynamically generate a noise floor using a noise signal, the noise floor being an estimate of noise level in the signal frequency band, the noise estimation circuit including a noise filter adapted to produce the noise signal by filtering the filtered cardiac signal, the noise signal having a noise frequency band that is substantially different from the signal frequency band;
an event detection circuit coupled to the sensing circuit and the noise estimation circuit, the event detection circuit adapted to dynamically adjust a detection threshold using at least the filtered cardiac signal and the noise floor and to detect cardiac electrical events using the filtered cardiac signal and the detection threshold, the noise floor used as a minimum value of the detection threshold;
a therapy output circuit to deliver one or more cardiac therapies;
a control circuit coupled to the sensing circuit, the event detection circuit, and the therapy output circuit, the control circuit adapted to control the delivery of the one or more cardiac therapies using at least the detected cardiac electrical events; and
an implantable housing configured to contain the sensing circuit, the noise estimation circuit, the event detection circuit, the therapy output circuit, and the control circuit.

18. The device of claim 17, wherein the therapy output circuit comprises a pacing circuit to deliver pacing pulses.

19. The device of claim 17, wherein the therapy output circuit comprises a cardioversion/defibrillation circuit to deliver cardioversion/defibrillation pulses.

\* \* \* \* \*

UNITED STATES PATENT AND TRADEMARK OFFICE
CERTIFICATE OF CORRECTION

Page 1 of 1

PATENT NO.       : 8,798,742 B2
APPLICATION NO.  : 12/415619
DATED            : August 5, 2014
INVENTOR(S)      : Linder et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this
Eleventh Day of August, 2015

Michelle K. Lee
*Director of the United States Patent and Trademark Office*